United States Patent [19]

Forlani

[11] Patent Number: 5,077,229

[45] Date of Patent: Dec. 31, 1991

[54] MONOLITHIC CHEMICAL SENSOR OF THE CHEMFET TYPE INCORPORATING AN ION-SELECTIVE MEMBRANE AND METHOD OF MAKING THE SAME

[75] Inventor: Franco Forlani, Milan, Italy

[73] Assignee: Eniricerche S.p.A., Milan, Italy

[21] Appl. No.: 417,237

[22] Filed: Oct. 5, 1989

[30] Foreign Application Priority Data

Oct. 10, 1988 [IT] Italy .................................. 67905 A/88

[51] Int. Cl.$^5$ ...................... H01L 21/00; H01L 21/02; H01L 21/230
[52] U.S. Cl. ........................................ 437/40; 437/41; 357/25; 324/71.5; 204/416; 204/418
[58] Field of Search ...................... 437/40, 41; 357/25; 324/71.5; 204/416, 418

[56] References Cited

U.S. PATENT DOCUMENTS

| | | | |
|---|---|---|---|
| 4,020,830 | 5/1977 | Johnson et al. | 357/25 |
| 4,269,682 | 5/1981 | Yano et al. | 204/418 |
| 4,305,802 | 12/1981 | Koshiishi | 204/418 |
| 4,411,741 | 10/1983 | Janata | 324/71.5 |
| 4,502,938 | 3/1985 | Covington et al. | 204/416 |
| 4,512,870 | 4/1985 | Kohara et al. | 204/418 |
| 4,636,827 | 1/1987 | Rudolf | 204/416 |
| 4,637,861 | 1/1987 | Krull et al. | 204/418 |
| 4,638,346 | 1/1987 | Inami et al. | 357/25 |
| 4,644,380 | 2/1987 | Zemel | 204/418 |
| 4,773,970 | 9/1988 | Purbrick et al. | 357/25 |
| 4,777,019 | 10/1988 | Dandekar | 324/71.5 |
| 4,874,499 | 10/1989 | Smith et al. | 204/416 |
| 4,883,767 | 11/1989 | Gray et al. | 437/41 |
| 4,960,722 | 10/1990 | Ogawa | 437/40 |

FOREIGN PATENT DOCUMENTS

| | | | |
|---|---|---|---|
| 0339613 | 11/1989 | European Pat. Off. | 204/418 |
| 0125776 | 11/1978 | Japan | 437/41 |
| 0082451 | 6/1980 | Japan | 437/41 |
| 0027067 | 2/1982 | Japan | 437/40 |
| 0181955 | 8/1986 | Japan | 204/418 |
| 0232250 | 9/1989 | Japan | 204/418 |
| 0277746 | 11/1989 | Japan | 324/71.5 |
| 2160356 | 12/1985 | United Kingdom | 324/71.5 |

OTHER PUBLICATIONS

Bergveld, P., "The Impact of MOSFET-Based Sensors", pp. 105–127, Sensors and Actuators, 8(1985).
Hanazato, Y., "Integrated Multi-Biosensors Based on an Ion-Sensitive Field-Effect Transistor Using Photolithographic Techniques", pp. 1303–1310, IEEE Trans. on Elect. Dev., vol. 36, No. 7, Jul. 1989.
Ito, T., "ISFET's With Ion-Sensitive Membranes Fabricated by Ion Implantation", pp. 56–64, IEEE Trans. on Elect. Dev., vol. ED-35, No. 1, Jan. 1988.
Esashi, M., "Biomedical Cation Sensor Using Field Effect of Semiconductor", pp. 339–343, Jour. of Jap. Soc. of Appl. Phys., vol. 44, 1975.

Primary Examiner—Brian E. Hearn
Assistant Examiner—B. Everhart
Attorney, Agent, or Firm—Rosen, Dainow & Jacobs

[57] ABSTRACT

The sensor comprises a chip of a semiconductor material wherein a field-effect transistor is formed the drain and source regions whereof are provided on a first face of the chip, onto which an ion-selective membrane is applied which is coupled to said field-effect transistor.

The membrane covers said first face of the chip completely, and terminals are provided in addition which comprise conductive elements applied to the other face of the chip and being connected to said drain and source regions by connections which extend through the chip.

These connections are formed by a method providing for the formation in the chip of buried layers of semiconductor material.

5 Claims, 3 Drawing Sheets

MONOLITHIC CHEMICAL SENSOR OF THE CHEMFET TYPE INCORPORATING AN ION-SELECTIVE MEMBRANE AND METHOD OF MAKING THE SAME

DESCRIPTION

This invention relates to a monolithic chemical sensor of the CHEMFET kind incorporating an ion-selective membrane. More specifically, the invention relates to a sensor which comprises, a chip of a semiconductor material, wherein a field-effect transistor (FET) is formed the drain and source regions whereof are formed on a first face of the chip and connected to terminals for connection to external circuits, and an ion-selective membrane applied on the chip and being coupled to the gate of said field-effect transistor.

In CHEMFET sensors manufactured by conventional techniques, the terminals of the field-effect transistor are made accessible (for the purpose of connecting the sensor to external circuits) on the same face of the chip on which the ion-selective membrane is deposited. Accordingly, that membrane can only cover a portion of said chip face. The consequent need for bounding in an accurate manner that area of the chip face which is to be covered by the membrane poses some formidable problems, both on account of the costs involved by the use of photolithographic techniques with organic materials for the membrane deposition, and of particular techniques made necessary for the sensor packaging.

It is the object of this invention to provide a monolithic membrane-type chemical sensor as specified above, which exhibits none of the problems with which prior sensors are beset.

This object is achieved, according to the invention, by a chemical sensor as indicated being characterized in that the membrane is arranged to cover the aforesaid first face of the chip completely, and that said terminals comprise conductive elements applied on the other face of the chip and being connected to said drain and source regions by connections which extend through the chip.

The invention is also concerned with a method of making a sensor of the type specified above, as set forth in the appended claims.

Further features and advantages of the invention will be more clearly understood from the following detailed description, to be read in conjunction with the accompanying non-limitative drawings, where:

Figure 1:
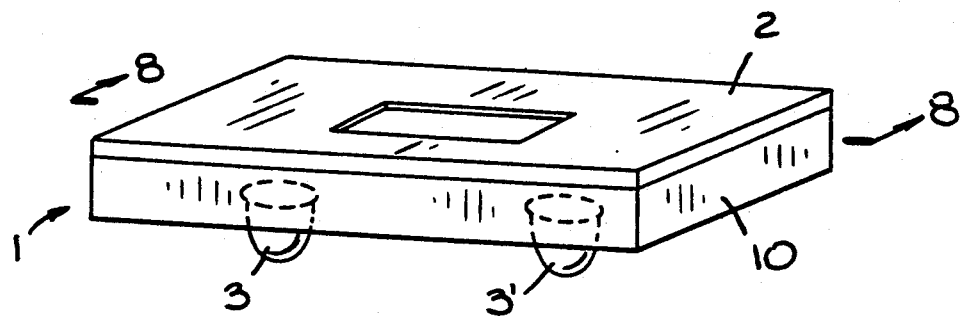
FIG. 1 is a perspective view of a CHEMFET-type chemical sensor according to the invention.

With reference to FIG. 1, a CHEMFET sensor according to the invention comprises a chip 1 of a semiconductor material, in particular silicon, wherein a field-effect transistor (FET) is formed (in a manner to be explained hereinafter). The drain and source regions of this transistor are formed on the upper face of the chip, to which an ion-selective membrane 2 is also applied. This membrane is coupled to the gate electrode of the field-effect transistor and completely covers the upper face of the chip 1.

The drain and source regions of the sensor field-effect transistor are connected to connection terminals 3, 3' consisting of conductive elements which are connected to said drain and source regions by connections extending through the chip 1. The features, and the procedures for making such connections through the chip will be described in detail herein below with reference to the drawing views.

The conductive elements 3, 3' may be "balloons" of Cu-Sn such as are used to make terminals for the so-called flip-chips.

With the above-described sensor, none of the complicated and cost-intensive photolithographic techniques is required for applying the membrane 2 onto the chip 1. The sensor packaging, moreover, is made far simpler.

CHEMFET sensors of the type described above may be conveniently utilized to make "intelligent sensors" by the hybrid circuit technology, wherein several CHEMFET sensors (each carrying a selective membrane toward a different chemical species) would be grouped on an isolating substrate provided with an appropriate network of interconnecting conductors, and possibly, circuitry and devices for processing the signals being output by the CHEMFET sensors.

A method of making a CHEMFET sensor according to the invention will be now described with reference to FIGS. 2 to 8.

Figure 2:
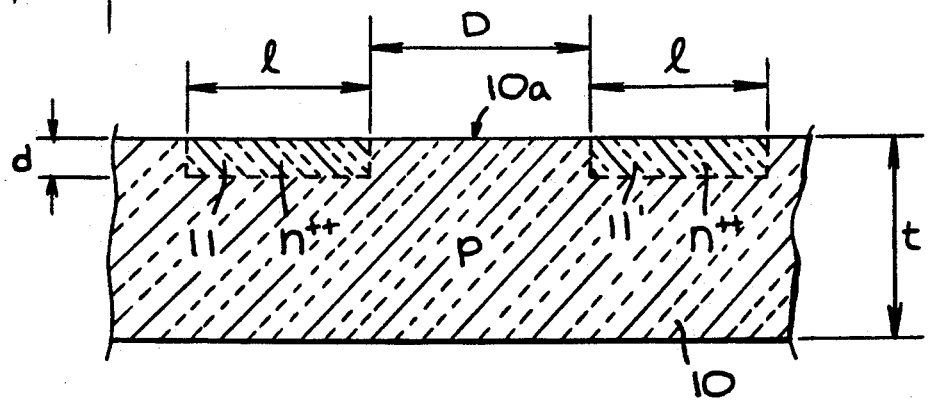
FIGS. 2 to 7 are fragmentary cross-sectional views taken through a semiconductor wafer at different stages of implementation of a method of making the sensor shown in FIG. 1.
Figure 3:
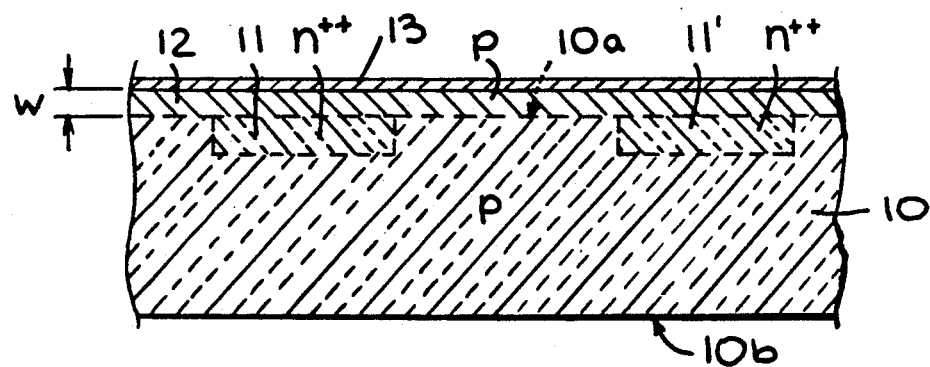

Shown at 10 in FIG. 2 is a wafer of a semiconductor material (silicon) having a p-type conductivity, for example. That wafer would preferably have a suitable orientation of its crystallographic axes (1 1 0) to facilitate successive preferential chemical attacks along a perpendicular direction to the major faces of the wafer.

Impurities having the opposite conductivity type from that of the monocrystalline wafer, i.e. of the $n^{++}$ type, are diffused through two adjacent surface regions 11, 11' of the upper face 10a of the wafer 10. The diffusion of such impurities is carried out over a long time period at a high surface concentration of the dopant.

By way of non-limitative example, the extent l of the regions 11 and 11' is in the 1 mm range, whilst their spacing or distance D apart is in the 50–70 $\mu m$ range. The depth of the regions 11, 11' the 5 $\mu m$ range.

Illustratively, the starting thickness dimension t of the silicon wafer is on the order of 150 $\mu m$.

A semiconductor layer 12 having the same p-type conductivity as the wafer 10 is then formed on the face 10a of the wafer 10 by epitaxial growth. The layer 12 may have a thickness w (FIG. 3) of about 4–5 $\mu m$.

Thereafter, the upper side of the layer 12 is passivated by thermal oxidation to form a thin oxide ($SiO_2$) layer effective to protect the layer 12 during the following process steps.

On completion of the layer 12, the regions 11, 11' will provide two "buried" layers.

Figure 4:
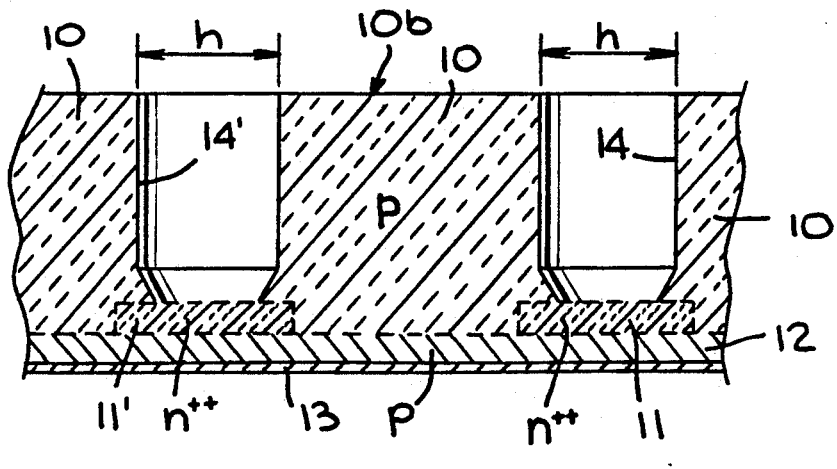

Using micromachining techniques, two pits (14,14') are then dug from the other major face 10b of the wafer 10 in directions toward the buried layers 11, 11' until said layers are exposed (FIG. 4). The pits may have a diameter dimension of about 0.8 mm.

In order to locate the areas on the face 10b where the pits 14, 14' should be dug, simple geometric references may be used or conventional alignment techniques such as by cross illumination in the infrared range.

The surface of the face 10b of the wafer 10 and the surfaces of the side and bottom walls of the pits 14, 14' are then subjected to thermal oxidation so as to form a layer 15 (FIG. 5) of SiO$_2$ which may have a thickness of 0.5 to 1.0 μm.

Figure 5:
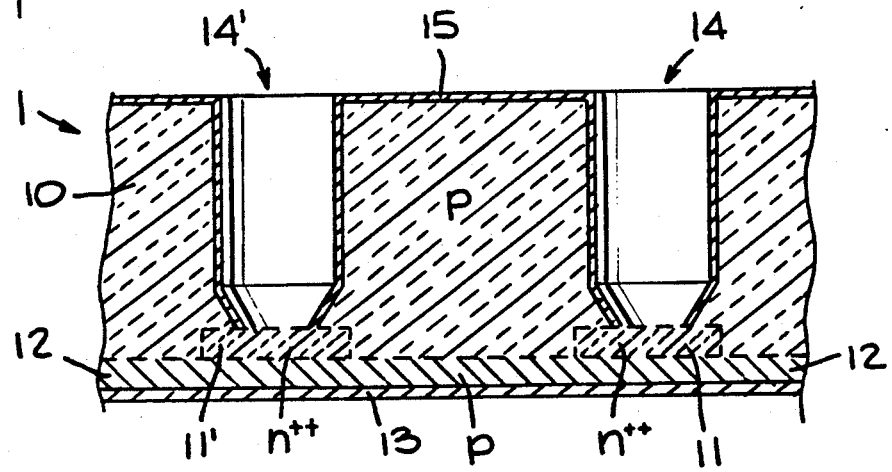
Figure 6:
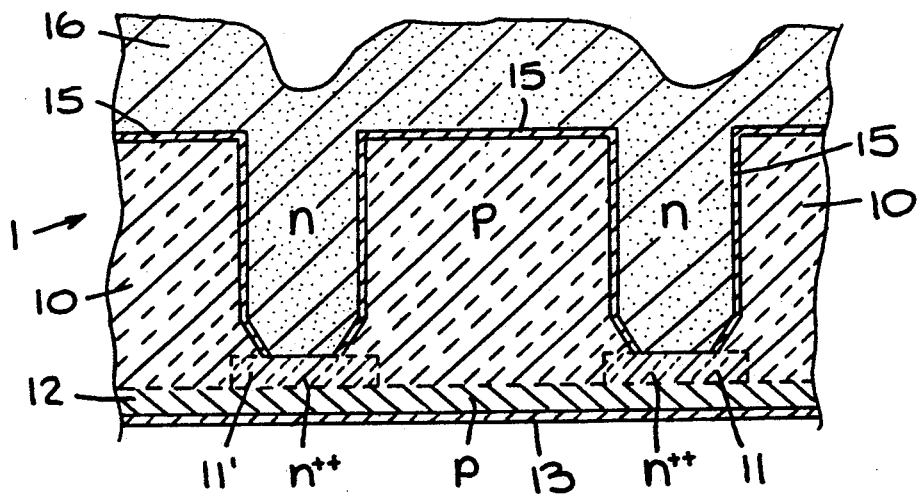

By directional plasma etching, for example, the oxide layer 15 is next removed from the bottom walls of the pits 14 and 15 to expose the buried layers 11, 11' as shown in FIG. 5.

Over the oxide layer 15 and the interiors of the pits 14, 14', a deposit of n-type conductivity silicon, as doped to degeneracy, is then formed which growths polycrystalline throughout except for the formation of any dendritic structures at the buried layers 11, 11'.

Figure 7:
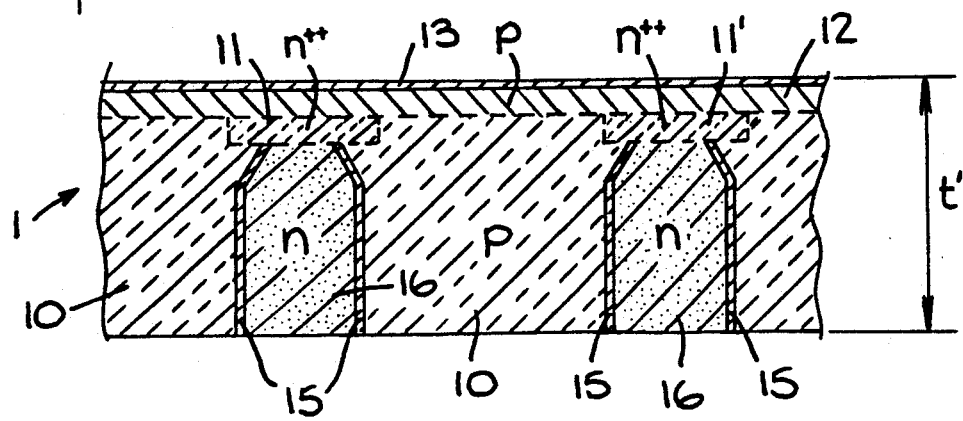

Excess polycrystalline silicon 16 is then removed to leave the monocrystalline silicon exposed around the pits 14, as shown in FIG. 7. The removal may be performed by a lapping step whereby the chip thickness is reduced to a value t' (FIG. 7) equal illustratively to 130-140 μm.

Figure 8:
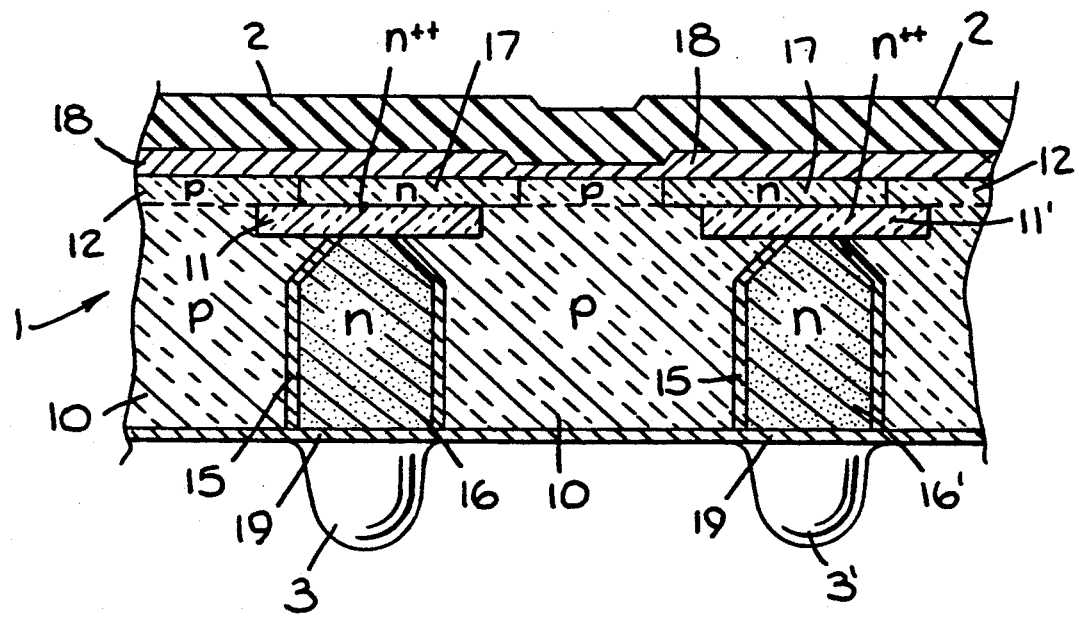
FIG. 8 is a fragmentary cross-sectional view taken along the line VIII—VIII of FIG. 1, showing the structure of an inventive sensor.

The SiO$_2$ layer 13 is removed, and n-type impurities are diffused in two regions of the epitaxial layer 12 indicated at 17, 17' in FIG. 8, as far down as the buried layers 11, 11'.

The regions 17 and 17' constitute the source and drain for the field-effect transistor of the sensor. That portion of the epitaxial layer 12 which extends between the regions 17 and 17' has p-type conductivity and constitutes the field-effect transistor channel.

Thereafter, an oxide surface layer 18 (FIG. 8) is formed once again over the layer 12 which may have a calibrated small thickness in the area overlying the channel of the field-effect transistor. The substrate 18 is then applied the ion-selective membrane 2.

The underside surface of the chip is then oxidized but for the surfaces of the polycrystalline silicon portions 16, which are instead provided with respective metalizations 19. The terminals 3 are applied to such metalizations.

Thus, the terminals 3, 3' are connected to regions 17 and 17' of the field-effect transistor through the bodies of n-type polycrystalline silicon 16 and the buried layers 11 and 11', respectively.

The above-described process enables a number of sensors to be formed on one silicon wafer; with a wafer having a diameter dimension of 5" (12.7 cm), approximately 500 to 600 chips can be provided in the 4×4 mm$^2$ size.

It stands to reason that, based upon this invention principle, the embodiments and implementation details may be significantly changed from what has been described herein and illustrated merely by way of non-limitative example, without departing from the scope of the invention.

As an example, comparable results may be obtained from a semiconductor wafer value with n-type conductivity, by providing p-type buried layers, filling the pits 14, 15 with polycrystalline semiconductor also of the p type, etc.

We claim:

1. A method of making a selective membrane, monolithic chemical sensor of the CHEMFET kind, comprising a chip formed from a monocrystalline semiconductor wafer having a specified type of conductivity wherein a FET-type transistor is formed and wherein the selective membrane is applied to one face of the chip and coupled to the gate of said transistor, characterized in that it comprises the steps of, diffusing an impurity having conductivity of an opposite type from that of the monocrystalline wafer in two adjacent surface regions of a first face of said wafer, forming as by epitaxial growth a semiconductor layer having the same type of conductivity as the wafer on said first face of the wafer, said two regions providing two buried layers;

making two pits in the other face of the wafer along directions toward the buried layers until said layers become exposed, forming a coating of an electrically insulative material on the surfaces of said other face of the wafer and of said pits to leave said buried layers exposed, filling said pits with a polycrystalline semiconductor material having opposite conductivity from that of the wafer, lapping said other face of the wafer to thereby remove excess polycrystalline semiconductor material and expose the surrounding monocrystalline semiconductor material, diffusing impurities of the same conductivity type as the buried layers in two regions of said epitaxial layer as far as said buried layers to provide the source and drain of a FET transistor, forming, on the surface of said epitaxial layer a layer of an electrically insulative material and then depositing the selective membrane onto said insulating layer, and applying terminal connection elements of an electrically conductive material to the surfaces of the polycrystalline material which fills said pits, said terminal elements protruding from said second face of the wafer.

2. A method according to claim 1, characterized in that said epitaxial layer is passivated by surface thermal oxidation for surface protection during the following process steps, the surface layer of oxide thus formed being removed prior to the impurity diffusing step whereby the drain and source of the field-effect transistor are formed.

3. A method according to either claim 1 or 2, characterized in that the insulating coating on said second face of the wafer and said pits comprises an oxide layer formed by thermal surface oxidation of the monocrystalline semiconductor material, and that the surface of said buried layers is then exposed by local plasma etching of said oxide layer.

4. A method according to any of the preceding claims, characterized in that the layer of electrically insulative material whereon the ion-selective membrane is deposited has a reduced calibrated thickness above that portion of the epitaxial layer which acts as the channel for the transistor (FET).

5. A method according to claim 1, characterized in that the surfaces of the polycrystalline semiconductor portions on said second face of the wafer are metalized prior to applying said terminal connection elements.

* * * * *